(12) United States Patent
Chu et al.

(10) Patent No.: US 7,073,289 B2
(45) Date of Patent: Jul. 11, 2006

(54) PROCESS FOR PRODUCING ORCHID SEEDLINGS BY STATIC LIQUID CULTURE

(76) Inventors: Chien-Young Chu, No. 94-3, Kong Lee St., South Dist., Taichung City (TW); Wei-Ting Tsai, No. 9-2, Lane 26, Wu-Chuan W. 5th St., Hsi Dist., Taichung City (TW)

( * ) Notice: Subject to any disclaimer, the term of this patent is extended or adjusted under 35 U.S.C. 154(b) by 136 days.

(21) Appl. No.: 10/957,736

(22) Filed: Oct. 5, 2004

(65) Prior Publication Data
US 2005/0086860 A1    Apr. 28, 2005

(30) Foreign Application Priority Data
Oct. 28, 2003   (TW) .............................. 92129959 A

(51) Int. Cl.
*A01H 4/00*   (2006.01)
(52) U.S. Cl. .................................. 47/58.1 R
(58) Field of Classification Search .................. None
See application file for complete search history.

(56) References Cited

U.S. PATENT DOCUMENTS

| | | | | |
|---|---|---|---|---|
| 5,656,482 | A * | 8/1997 | Knorr et al. ................ | 435/410 |
| 5,864,985 | A * | 2/1999 | Zhou ......................... | 47/62 N |
| 6,060,313 | A * | 5/2000 | Zhou et al. ................. | 435/420 |
| 6,168,952 | B1 * | 1/2001 | Oh et al. .................... | 435/430 |
| 6,924,143 | B1 * | 8/2005 | Aichinger et al. .......... | 435/383 |
| 2003/0172426 | P1 * | 9/2003 | van Rijsselberghe | |
| 2005/0050592 | A1 * | 3/2005 | Gray et al. ................. | 800/295 |
| 2005/0086860 | A1 * | 4/2005 | Chu et al. .............. | 47/58.1 SC |

OTHER PUBLICATIONS

Von Arnold, et al., "Effect of agar concentration on growth and anatomy of adventitious shoots of *Picea abies* (L.) Karst.", Plant Cell Tissue-Organ Culture, vol. 3, pp. 257-264, 1984.

Debergh, et al., "A Scheme for Commercial Propagation of Ornamental Plants by Tissue Culture", Scientia Horticulturae, 14 (1981), pp. 335-345.

Bornman, et al., "Effect of rigidity of gel medium on benzyladenine-induced adventitious bud formation and vitrification in vitro in *Picea abies*", Physiol. Plant. vol. 61, pp. 505-512, 1984.

(Continued)

*Primary Examiner*—Francis T. Palo
(74) *Attorney, Agent, or Firm*—Sughrue Mion, PLLC

(57) ABSTRACT

Disclosed herein is a process for producing orchid seedlings by static liquid culture, in which a suitable amount of orchid seeds are suspended in a liquid medium suitable for the germination and growth of the orchid seeds to form a seed suspension; the seed suspension is then added into an empty culture container, so that the seed suspension within the culture container has a predetermined depth sufficient to enable each of the seeds to be suspended within the liquid medium while not causing said each seedling to an oxygen-deficient state; thereafter, the container is allowed to stand, such that the seeds suspended within the liquid medium germinate and grow into seedlings. The young seedlings thus obtained can be further cultivated by static liquid culture.

14 Claims, 11 Drawing Sheets
(8 of 11 Drawing Sheet(s) Filed in Color)

OTHER PUBLICATIONS

Douglas, "Propagation of Eight Cultivars of Rhododendron in Vitro Using Agar-Solidified and Liquid Media and Direct Rooting of Shoot in Vivo", Scientia Horticulturae, 24 (1984), pp. 337-347.

Viseur, "Mircropropagation of Pear, Pyrus Communis L., In a Double-Phase Culture Medium", Acta Horticulturae, 212, 1987, pp. 117-124.

Paques, et al., "Liquid Media to Improve and Reduce the Cost of In Vitro Conifer Propagation", Acta Horticulturae, 310, 1992, pp. 95-100.

Etienne, et al., "Temporary immersion systems in plant micropropagation", Plant Cell, Tissue and Organ culture, vol. 69, pp. 215-231, 2002.

Zhou, "In vitro culture of Doritaenopsis: comparison between formation of the hyperhydric protocorm-like-body (PLB) and the normal PLB", Plant Cell Reports, vol. 15, pp. 181-185, 1995.

Takayama, et al., "Mass Propagation of Begonia X hiemalisPlantlets by Shake Culture", Plant & Cell Physiol, 22(3): 461-467 (1981).

Ziv, et al., "Scaled-up proliferation and regeneration of Nerine in liquid cultures Part I. The induction and maintenance of proliferating meristematic clusters by paclobutrazol in bioreactors", Plant Cell, Tissue and Organ Culture, vol. 39, pp. 109-115, 1994.

Lilien-Kipnis, et al., "Scaled-up proliferation and regeneration of Nerine in liquid cultures Part II. Ontogeny of somatic embryos and bulblet regeneration", Plant Cell, Tissue and Organ Culture, vol. 39, pp. 117-123, 1994.

Onishi, et al., "Synthetic seeds as an application of mass production of somatic embryos", Plant Cell, Tissue and Organ Culture, vol. 39, pp. 137-145, 1994.

Osuga, et al., "Synchronization of somatic embryogenesis from carrot cells at high frequency as a basis for the mass production of embryos", Plant Cell, Tissue and Organ Culture, vol. 39, pp. 125-135, 1994.

Luttman, et al., "Silicone-tubing aerated bioreactors for somatic embryo production", Plant Cell, Tissue and Organ Culture, vol. 39, pp. 157-170, 1994.

Adelberg, et al., "Orchid Micropropagation on Polypropylene Membranes", American Orchid Society Bulletin, Jul. 1992, 688-695.

Adelberg, et al., "Long-term nutrient and water utilization during micropropagation of Cattleya on a liquid/membrane system", Plant Cell, Tissue and Organ Culture, vol. 48, pp. 1-7, 1997.

Lakshmanan, et al., "An in vitro method for rapid regeneration of a monopodial orchid hybrid Aranda Deborah using thin section culture", Plant Cell Reports, vol. 14, pp. 510-514, 1995.

Young, et al., "Mass multiplication of protocorm-like bodies using bioreactor system and subsequent plant regeneration in Phalaenopsis ", Plant Cell, Tissue and Organ Culture, vol. 63, pp. 67-72, 2000.

Phan, et al., "Possible metabolic basis for the developmental anormaly observed in in vitro culture, called 'vitreous plants'", Plant Cell, Tissue and Organ Culture, vol. 6, pp. 83-94, 1986.

Tsai, et al., "An Important Factor Affecting the Germination and Growth of Phalaenopsis Seeds", The SABRAO International Symposium on The Impact of Biological Research on Agricultural Productivity, pp. 219-228, 1992.

Murashige, et al., "A Revised Medium for Rapid Growth and Bio Assays with Tobacco Tissue Cultures", Physiologia Plantarum, vol. 15. pp. 473-497, 1962.

* cited by examiner

PROCESS FOR PRODUCING ORCHID SEEDLINGS BY STATIC LIQUID CULTURE

CROSS-REFERENCE TO RELATED APPLICATION

This application claims priority of Taiwan Patent Application No. 092129959, filed on Oct. 28, 2003.

BACKGROUND OF THE INVENTION

1. Field of the Invention

The invention relates to a process for producing orchid seedlings, in particular the seedlings of moth orchids (genus *Phalaenopsis*), by static liquid culture, in which orchid seeds are suspended in a liquid medium suitable for the germination and growth thereof, and the depth of the thus obtained seed suspension in a culture container is set to be within a predetermined range at the onset of culture.

2. Description of the Related Art

The major export crops of Taiwan are orchids, in particular moth orchids (genus *Phalaenopsis*). Orchids are not only the number one export commodity of Taiwan, they are also very popular in Taiwan's domestic market. In Taiwan, over 90 million seedlings of *Phalaenopsis* are produced each year, of which 60% are seedlings developed from seeds. The business of breeding orchid seedlings is therefore a very lucrative one. However, in order to maintain dominance in the export market, the techniques of tissue culturing orchid seedlings have to be improved so as to lower costs and upgrade quality.

At present, solidified agar media are used in the production of orchid flask seedlings. Agar accounts for about 30–40% of the cost of the culture medium materials, and is the most expensive ingredient of the culture medium formulas. Besides, the step of melting agar is the most time-consuming procedure in the preparation of the medium. In addition, in the cultivation of orchid seedlings, sowing of seedlings in vitro is still the most widely used method of production. However, the seedling production processes are largely traditional. For instance, glass flasks with rubber stoppers, which do not provide good ventilation, are used as culture containers. In addition, high density sowing and high density subculture are adopted in the culture of seedlings. Non-uniform growth of seedlings is a common phenomenon on a production line that adopts the traditional seedling production process, and multi-stage screening is therefore required. During the process of subculturing, oftentimes, many smaller seedlings have to be discarded, resulting in a waste of seedlings and higher labor costs. Therefore, improving the seedling production process is an important factor to be taken into consideration in the attempt to reduce orchid seedling production costs.

Furthermore, it is reported that agar, when used as a gelling agent to prepare a solid culture medium, will affect the osmotic potential of the culture medium, thereby affecting the absorption of nutrients by an explant (von Arnold and T Eriksson (1984), *Plant Cell, Tissue and Organ Culture*, 3:257–264). In other studies, it has been pointed out that the amount of cytokinin absorbed by an explant is in an inverse correlation with the rigidity of the gel of the culture medium (Debergh, P. C. and L. J. Maene (1981), *Sci. Hort.*, 14:335–345; Bomman, C. H. and T. C. Vogelmann (1984), *Physiol. Plant.*, 61:501–512), thereby affecting the multiplication rate.

Liquid culture has been proven to be capable of achieving an explant multiplication rate higher than that achievable by solid culture for many plants, such as roses (Chu, C. Y., M. Y. Wang (1995), "*Effect of culture medium on growth of tissue-cultured explants*," *Journal of Agriculture and Forestry*, 44 (4):71–77), rhododendrons (Douglas, G. C. (1984), *Sci. Hort.*, 24: 337–347), pears (Viseur, J. (1987), Acta Hort., 212: 117–124), and conifers (Pâques, M. J. et al. (1992), *Acta Hort.*, 319: 95–100), etc.

However, plant seedlings are susceptible to hyperhydricity (or vitrification) after being grown in a liquid medium for a long time (Etienne, H. and M. Berthouly (2002), *Plant Cell, Tissue and Organ Culture*, 69: 215–231). Many studies showed that once an explant was observed to develop hyperhydricity, it was difficult to recover the explant to its normal state. Although increasing the rigidity of the culture medium is an effective way to restore the hyperhydric explant to its normal state, it is not suitable for certain plants, such as protocorm-like-bodies (PLBs) of *Doritaenopsis* (Zhou, T. S. (1995), *Plant Cell Reports*, 15:181–185).

The use of a liquid medium in conjunction with shaking, rotation or direct aeration of the culture medium to propagate plants was proposed in the cultivation of *Begonia×hiemalis* in the early years (Takayama, S. et al. (1981), *Plant and Cell Physiol.*, 22:461–467). In the recent decades, there have been reports on the successful propagation of other plants, such as lilies (Takayama, S. et al. (1991), *Automated propagation of microbulbs of lilies*. In: Wasil I K (Ed.) *Cell Culture and Somatic Cell Genetics of Plants*. Vol. 8:111–131. Academic Press, Inc.), Nerine (Ziv, M. et al. (1994), *Plant Cell, Tissue and Organ Culture*, 39:109–115; Lilien-Kipnis, H. et al. (1994), *Plant Cell, Tissue and Org. Cult.*, 39:117–123), carrots (Onishi, N. et al. (1994), *Plant Cell, Tissue and Org. Cult.*, 39:137–145; Osuga, K. et al. (1994), *Plant Cell, Tissue and Org. Cult.*, 39:125–135) and *Euphorbia pulcherrima* (Luttman, R. et al. (1994), *Plant Cell, Tissue and Org. Cult.*, 39:157–170).

As for orchids, there are reports pointing out that the use of liquid culture can increase the rate of proliferation of protocorms (Adelberg, J. W. et al., (1992), *Amer. Orch. Soc. Bull.*, 61:688–695; Adelberg. J. W. et al. (1997), *Plant Cell, Tissue Org. Cult.*, 48:1–7); Lakshmanan, P. et al. (1995), *Plant Cell Rep.*, 14:510–514; Young, P. S. et al. (2000), *Plant Cell, Tissue and Org. Cult.*, 63:67–72). However, proliferation of protocorms from seedlings has to be avoided so as not to delay differentiation of leaves and so as not to result in mutation of the variety, which may affect assessment of the offspring trait distribution. At present, the applicants are not aware of any study or report on the production of orchid seedlings by sowing in a static liquid suspension.

Occurrence of vitrification in explants is mainly caused by an increase in the water potential. That is, an increase in the water usable by the explant leads to fast abnormal growth so that the explant lacks lignin and cuticle, thereby resulting in a glassy appearance, and the content of chlorophyll drops, thereby resulting in production of ethylene (Phan, C. T. and P. Hegedus (1986), *Plant Cell Tissue and Org. Cult.*, 6:83–94). High cytokinin concentration and low agar concentration will also promote generation of vitrificated explants. Although addition of phloroglucinol reagent to the culture medium (Phan, C. T. and P. Hegedus (1986), supra), or use of cold treatment (Boxus, P. (1978), *Rapport d'Activite Compter Rendus, Gembloux, Belgique*. pp. 126–127) is capable of restoring the vitrified explant to normal growth, the best way is to lower the concentration of cytokinin and increase the amount of agar or to increase air circulation in the vessel so as to prevent production of vitrified explants (Pasqualetto, M. et al. (1986), *Acta Hort.*, 319: 95–100). In the production of flask seedlings of *Phalaenopsis*, since there is no need for proliferation of protocorms, cytokinin is rarely used. Therefore, if a liquid medium is to be used to culture flask seedlings, the water potential and the air ventilation of the culture container must be considered.

At present, solid culture media are widely used for the production of flask seedlings of *Phalaenopsis*, and glass flasks are used as culture containers, which are sealed by a rubber stopper with a hole plugged by cotton wool. Take the production of *Phalaenopsis* seedlings as an example. Flask transfer of the seedlings has to be conducted for at least two times after seed sowing, and it would take around one year before the seedlings can be removed from the flasks for planting. Since cultivation of flask seedlings of *Phalaenopsis* requires three to four times of flask transfer operations, which account for about 65–70% of the labor cost, if the flask transfer operations in the seedling production can be simplified, or the labor costs needed for conducting one to two times of flask transfer can even be dispensed with, the production costs can be reduced considerably. Furthermore, if a liquid medium is used to culture orchid flask seedlings, since solidification of the culture medium is not required, the preparation cost can be lowered. Moreover, the use of a liquid medium to produce orchid seedlings can result in uniform growth of the flask seedlings, which facilitates the grading of seedlings in the subsequent subculturing process, and simplifies and speeds up the operating procedures of subculturing, thereby reducing labor costs and upgrading the quality of flask seedlings. Therefore, if the problem of vitrification associated with the use of liquid media can be overcome, the competitive edge of orchid flask seedling production can be enhanced to a large extent.

SUMMARY OF THE INVENTION

Therefore, one aspect of the present invention is to provide a process for producing orchid seedlings by static liquid culture, which comprises:
(a) suspending a suitable amount of orchid seeds in a liquid medium suitable for germination and growth of the orchid seeds to form a seed suspension; and
(b) adding the seed suspension obtained in step (a) into an empty culture container having a bottom wall to allow the seed suspension within the culture container to have a predetermined depth sufficient to enable each of the seeds to be suspended within the liquid medium while not subjecting any seed closest to the bottom wall of the culture container to an oxygen-deficient state, for the suspended seeds to germinate and grow.

Subsequent to step (b) of the process according to this invention, a step (c) of subjecting the culture container to a standing treatment to allow the seeds suspended within the liquid medium to germinate and grow into seedlings may be conducted.

After being subjected to the standing treatment of step (c), the orchid seeds suspended within the liquid medium germinate and grow into seedlings having first leaves not larger than 0.4 cm. Thereafter, the seedlings are further cultivated by the following steps:
(d) placing the seedlings obtained in step (c) into a culture container having a bottom wall and containing a liquid medium suitable for growth of orchid seedlings such that the liquid medium in the culture container has a predetermined depth sufficient to enable each of the seedlings to be suspended in the liquid medium while not subjecting any seedling closest to the bottom wall of the culture container to an oxygen-deficient state; and
(e) allowing the culture container to stand such that the seedlings suspended in the liquid medium grow further.

After being subjected to the standing treatment of step (e), the seedlings obtained in step (c) grow into seedlings with two leaves.

The process according to this invention does not require agar, and can therefore save culture medium material costs by 30–40%. Moreover, the process according to this invention does not require melting of the agar, thereby simplifying the process of preparing the culture medium. It is estimated that more than 30% of the preparation time and the energy required for heating can be saved. Furthermore, since the liquid medium can contact the seeds uniformly, the nutrient absorption rate of the seeds can be increased. Thus, the amount of the liquid medium used can be considerably lower than that of a solid culture medium. Because the amount of liquid medium is small, manufacturers in the art can conduct initial culture using flat containers. Thus, the culture containers can be stacked to thereby increase the space utilization efficiency of the culture room. In addition, subculturing of the seedlings grown in liquid medium can be easily carried out to thereby enhance labor efficiency.

It has been proven that, as compared to the seedlings grown in conventional solid culture media, the seedlings cultured according to the process of this invention have more uniform growth, faster growth, and increased dry weight/fresh weight ratios. Besides, the culture period of the seedlings can be shortened by more than 1.5 months. In addition, the process according to this invention not only can simplify seedling transfer operation, since the seedlings are uniform, the number of seedling transfer operations can be reduced to considerably lower production costs and to upgrade seedling quality. Therefore, there would be large profit margins for manufacturers in the art using the process of this invention.

BRIEF DESCRIPTION OF THE DRAWINGS

The patent or application file contains at least one drawing executed in color. Copies of this patent or patent application publication with color drawings will be provided by the Office upon request and payment of the necessary fee.

Other features and advantages of the present invention will become apparent in the following detailed description of the preferred embodiment with reference to the accompanying drawings, of which.

DETAILED DESCRIPTION OF THE PREFERRED EMBODIMENTS

Figure 1:
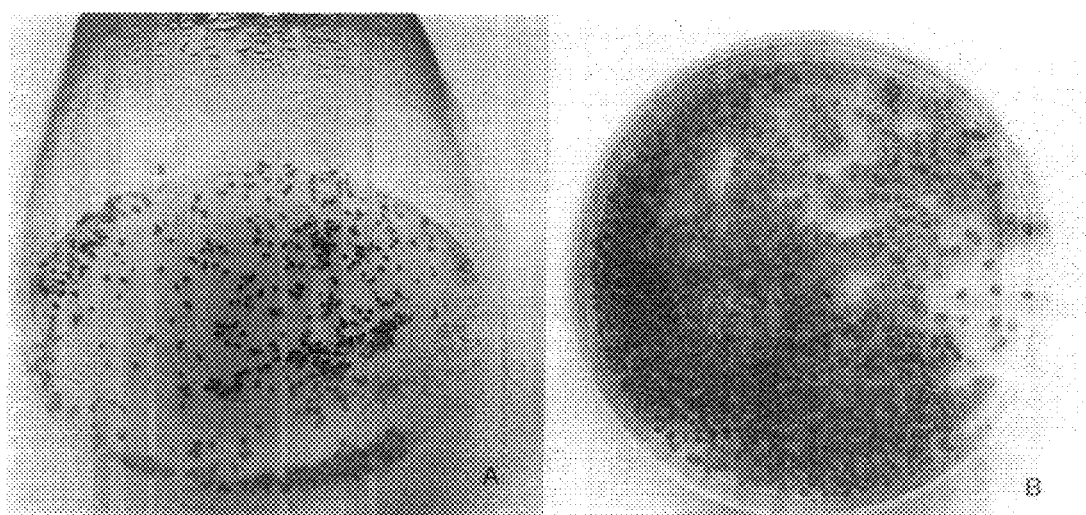
FIG. 1 shows the growth results of *Phalaenopsis* seedlings 60 days after sowing of *Phalaenopsis* seeds in a solid culture medium and a liquid medium, respectively, in which the left panel (control group) shows seedlings grown in the solid culture medium, whereas the right panel (experimental group) shows seedlings grown in the static liquid culture according to this invention.

Since the development of sterile sowing techniques for producing orchid seedlings in the 1960s, the operation procedures thereof have scarcely been improved. At present, glass flasks with rubber stoppers, which do not permit good air ventilation, are still used as culture containers, and solid culture media prepared from agar gel are used to culture seedlings, which were developed from seeds under a high sowing density and then subjected to subculture for several times. However, orchid seedlings that are cultured using the conventional sowing techniques do not exhibit uniform growth, thereby necessitating several grading operations during subculturing and discarding of many smaller seedlings, which not only is a waste of resources but also increases production costs.

Liquid culture not only can reduce the cost of formulating culture media considerably, it also has been proven to achieve propagation and growth rates higher than those attainable with solid culture. The main difficulty encountered in liquid culture is associated with the supply of oxygen needed by the plants. Therefore, at present, liquid culture of non-orchid plants largely adopts supports in culturing. Alternatively, shaking or rotation is used in culturing, or the culture medium is aerated with oxygen. These methods result in not only increased equipment costs but also complicated culturing operations. Furthermore, these methods will result in proliferation of more protocorms, which is undesirable.

To improve the operating procedures for producing orchid seedlings and to upgrade seedling quality, the applicants attempted to substitute conventional solid culture with static liquid culture and to establish models for suspension sowing and subculturing.

The seeds of orchids are very small and do not contain endosperms therein. Therefore, media suitable for culturing orchid seeds have to be supplied with nutrients necessary for the germination and growth of said seeds. The problem of aeration also has to be taken into account when culturing orchid seeds in a liquid medium. The applicants' studies in relation to this invention were based on the following presumption: if the evolution of living creatures started in water, then orchid seeds sown in an aqueous environment should be able to adapt to the aqueous environment and survive. Accordingly, the applicants attempted to sow a suspension of orchid seeds in a culture container, followed by allowing the culture container to stand on a culture shelf. The sown seeds were then observed in terms of germination and growth.

In these studies, the applicants found that during the stage of initial culture, the orchid seeds could germinate and grow in a liquid medium in the absence of any support, such as a raft. The applicants also noted that the depth of the culture medium would affect the growth of orchid seeds sown therein. That is, although a greater depth of the culture medium will not affect the germination of the seeds, it will cause vitrification of the germinated seedlings. On the other hand, if the water level of the culture medium is too low, the culture medium will soon dry up, which requires frequent replenishment of water, thereby resulting in increased operation times. In addition, when an appropriate material is used to seal the culture container, a suitable culture medium depth can be maintained for the seeds to develop to a size suitable for conducting the next culture stage, and the growth of the orchid seedlings are faster and more uniform as compared to those grown in a solid culture. Therefore, finding a suitable depth of culture medium that can permit germination of seeds without further addition of water is a key factor that will affect the success of liquid sowing of orchid seeds.

Furthermore, as the amount of culture medium utilized in liquid sowing is far less than the amount of culture medium used in solid culture, the contents of nutrients in the culture medium may also be a factor affecting the growth of seedlings. It is known in literature that potato paste is an important ingredient affecting the germination and growth of *Phalaenopsis* seeds. In particular, potato paste can increase the survival rate of seedlings cultivated under a high density, and the addition of potato paste in the culture medium can reduce the occurrence of vitrificated protocorms (Tsai, W. T. et al. (1992), *An important factor affecting the germination and growth of Phalaenopsis seeds*. The SABRAO International symposium on the impact of biological research on agricultural productivity. pp. 219–228). Nevertheless, the addition of potato starch in a culture medium for orchid seeds failed to provide such an effect (Zhou, T. S. (1995), *Plant Cell Rep.*, 15:181–185).

However, in the preparation of a liquid medium, potato paste can increase the viscosity of the culture medium to thereby affect the operation adversely. Therefore, in order to enable orchid seeds to adapt to liquid suspension culture, the applicants further found out the sowing density and the components of the culture medium which are suitable for liquid culture, so as to increase survival rate and reduce occurrence of vitrification. In studies relating to this invention, the applicants discovered that the growth rate of orchid seedlings would slow down with the rise in sowing density.

Subsequent to the appearance of first leaves on the orchid seedlings after liquid sowing, the applicants conducted liquid subculture. It was found that the shoots of seedlings cultured in liquid likewise exhibited faster and more uniform growth as compared to those grown in solid culture. That is, from sowing orchid seeds to transferring thus developed orchid explants onto a solid culture medium for rooting, the culture period could be shortened by 1.5 months or more with the use of a liquid medium as compared to the use of a conventional solid culture medium.

Accordingly, the applicants devised a process for producing orchid seedlings by static liquid culture. The process comprises the steps of:

(a) suspending a suitable amount of orchid seeds in a liquid medium suitable for germination and growth of the orchid seeds to form a seed suspension; and (b) adding the seed suspension obtained in step (a) into an empty culture container having a bottom wall to allow the seed suspension within the culture container to have a predetermined depth sufficient to enable each of the seeds to be suspended within the liquid medium while not subjecting any seed closest to the bottom wall of the culture container to an oxygen-deficient state, for the suspended seeds to germinate and grow.

As used herein, the term "oxygen-deficient state" refers to a condition that the depth of the seed suspension within the culture container renders an orchid seed suspended within the liquid medium unable to take up sufficient oxygen for growth.

Subsequent to step (b) of the process according to this invention, a step (c) of subjecting the culture container to a standing treatment to allow the seeds suspended within the liquid medium to germinate and grow into seedlings may be conducted.

According to this invention, the culture container is allowed to stand during the culture period. There is no need to perform rotation or shaking. Moreover, since the liquid medium has a predetermined depth, the seeds can have an adequate supply of oxygen to eliminate the need for additional aeration.

In a preferred embodiment of this invention, the process according to this invention is used for producing *Phalaenopsis* seedlings.

A liquid medium suitable for use in step (a) of the process according to this invention may be any culture medium suitable for germination and growth of orchid seeds. For instance, components of conventional solid culture media can be employed, but without addition of agar. The liquid medium may contain: basic salts, e.g., Knudson C. (1946) salts (Knudson, L. (1946), *Amer Orchid Soc. Bull.* 15: 214–217); sugars, e.g., sucrose; and natural ingredients, e.g., potato paste. Common orchid culture media include MS (Murashige, T. and Skoog F. (1962), *Physiol. Plant.*, 15, 473–497), V. W, Knudson C, and Kyoto formulation (Chu, C. C. (1988), *Sowing and tissue culture of Phalaenopsis*, Yanglan Magazine Publication).

In a preferred embodiment of the present invention, the culture container used in step (b) of the process according to this invention is a petri dish with a cover.

Preferably, in step (b) of the process according to this invention, the seed suspension added into the culture container has a predetermined depth of no greater than 1 cm, as measured from the bottom wall of the culture container. In a preferred embodiment of the present invention, the seed suspension added into the culture container has a predetermined depth within a range from 0.1–1.0 cm as measured from a bottom wall of the culture container. In a more preferred embodiment of the present invention, the seed suspension added into the culture container has a predetermined depth within a range from 0.1–0.6 cm. In a most preferred embodiment of the present invention, the seed suspension added into the culture container has a predetermined depth within a range from 0.2–0.5 cm.

Preferably, the seed suspension prepared in step (a) of the process according to this invention has a seed sowing density of not greater than 113±9 seeds/ml culture medium. In a preferred embodiment of the present invention, the seed suspension added into the culture container has a seed sowing density of not greater than 75±6 seeds/ml culture medium. In a more preferred embodiment of the present invention, the seed suspension added into the culture container has a seed sowing density of not greater than 38±3 seeds/ml culture medium.

Orchid seeds are very tiny. For instance, a capsule of *Phalaenopsis* may contain tens of thousands of seeds, and there are about 500±50 seeds per milligram on the average. To facilitate determination of the seed sowing density, during culturing of orchid seeds, the quantity of the seeds is estimated by weight. Therefore, orchid seeds obtained from a capsule are first subjected to a viability test. Seeds tested to have a viability value over 90% are then selected and weighed for later use. When preparing a seed suspension having a desired seed sowing density, seeds of a corresponding weight may be taken.

Preferably, in the process according to this invention, an additional step of sealing the culture container with a sealing material is conducted between steps (b) and (c), so as to retard the evaporation of water from the seed suspension contained in the culture container. The sealing material may be any material which is suitable for sealing a tissue culture container, and can help regulate the evaporation of water from the culture medium and control the growth of orchid seedlings and the culture period of the same.

The sealing material suitable for use in the additional step of the process preferably includes sealing films of different air ventilating characteristics, and is more preferably selected from a group consisting of paraffin films, air-permeable tapes (e.g., 3M micropore™ tapes), and a combination thereof.

In a preferred embodiment of this invention, the culture container is first sealed with an air-permeable paraffin film for a period of time, followed by sealing with an air- and water-permeable 3M micropore™ tape for a further period of time, so that the seedlings can achieve better growth.

According to the process of this invention, after being subjected to the standing treatment of step (c), the orchid seeds that are suspended in the liquid medium germinate and grow into seedlings with first leaves not larger than 0.4 cm. In a preferred embodiment of this invention, it takes about 75 days for the orchid seeds to develop the first leaves after being subjected to the standing treatment for germination and growth.

According to this invention, seedlings having developed the first leaves in step (c) of the process are further cultivated by performing the following steps:

(d) placing the seedlings obtained in step (c) into a culture container having a bottom wall and containing a liquid medium suitable for growth of orchid seedlings such that the liquid medium in the culture container has a predetermined depth sufficient to enable each of the seedlings to be suspended in the liquid medium while not subjecting any seedling closest to the bottom wall of the culture container to an oxygen-deficient state; and (e) allowing the culture container to stand such that the seedlings suspended in the liquid medium grow further.

Preferably, the culture container used in step (d) of the process according to this invention is a square-shaped tissue culture container, such as a Magenta GA7 culture container.

Preferably, in step (d) of the process according to this invention, the liquid medium contained in the culture container has a predetermined depth of not greater than 1.6 cm, as measured from the bottom wall of the culture container. In a preferred embodiment according to this invention, the liquid medium contained in the culture container has a predetermined depth within a range of 0.2 cm to 1.5 cm, as measured from the bottom wall of the culture container. In a more preferred embodiment according to this invention, the liquid medium contained in the culture container has a predetermined depth within the range of 0.3 cm to 1.0 cm, as measured from the bottom wall of the culture container. In a further preferred embodiment according to this invention, the liquid medium contained in the culture container has a predetermined depth within the range of 0.3 cm to 0.8 cm, as measured from the bottom wall of the culture container.

The liquid medium suitable for use in step (d) of the process according to this invention may be any culture medium suitable for growth of orchid seedlings. For instance, components of conventional solid culture media can be employed, but without the use of agar. The liquid medium may contain: basic salts, e.g., 1/4MS salts (Murashige et al. (1962), supra); sugar, e.g., sucrose; and natural ingredients, e.g., potato paste.

Preferably, in step (d) of the process according to this invention, the seedlings obtained in step (c) are placed in the liquid medium in the culture container at a sowing density within a range of about 1 to 8 seedlings/ml of culture medium. More preferably, the seedlings are placed in the liquid medium in the culture container at a sowing density within a range of about 1 to 5 seedlings/ml of culture medium.

Preferably, in step (d) of the process according to this invention, the seedlings obtained in step (c) are placed in a liquid medium in a culture container which does not have any support at the bottom thereof. Optionally, the seedlings obtained in step (c) may be placed in a liquid medium in a culture container which has a support disposed at the bottom thereof. The support may be a substrate conventionally used in tissue culture, such as filter paper, nonwoven fabric, a plastic raft with water-permeable film, a cellulose rod, or the like.

According to the process of this invention, after being subjected to the standing treatment of step (e), the seedlings obtained in step (c) develop into seedlings with about 2 leaves. In a preferred embodiment of this invention, it takes about 45 days for the seedlings obtained in step (c) to develop two leaves after being subjected to static liquid culture.

Preferably, in step (d) of the process according to this invention, the culture container is not sealed with any sealing material. Therefore, the water in the liquid medium will decrease due to evaporation so that the liquid medium does not have any flowable water after standing for a period of time. At this time, the seedlings have grown to an extent ready for the next stage of culture, and can be easily removed from the culture container for the next stage of culture, for instance, for placement in a liquid medium contained in a culture container which has a support placed at a bottom thereof, or for planting on a solid culture medium contained in a culture container.

Since the process of this invention is conducted merely by static liquid culture, as compared to conventional processes using solid culture, the orchid seedlings cultured according to this invention are mainly seedlings, with a rare formation of protocorms. Moreover, growth of the seedlings is fast and uniform, thereby remarkably upgrading production quality.

EXAMPLES

This invention will be described in greater detail by way of the following examples. However, it should be understood that the following examples are intended for the purpose of illustration only and should not be construed as limiting the scope of this invention.

For convenience of illustration, *Phalaenopsis* seeds were used to conduct experiments described in the Examples that are provided below for the purpose of illustration.

Example 1

The Effects of the Depth of a Liquid Medium Contained in a Culture Container, the Manner of Sealing the Culture Container, and the Medium Components upon the Growth of Orchid Seeds in Static Liquid Culture I. Plant Material:

Unopened 4.5 month-old capsules of Dtps. (Tinny Antique×Sinica Peeress)×Dtps. Sogo Beach were used as the material. The surfaces of the capsules were sterilized with a 2% sodium hypochlorite solution for 10 minutes. The capsules were then rinsed in sterile water for three times before being cut open, and the opened capsules were tapped to obtain the seeds. The seeds were stained with a staining solution containing 0.5% triphenyl tetrazolium chloride (TTC) at room temperature for 24 hours to verify the viability thereof. It was found after calculation that there were about 500±50 seeds per milligram of seeds having a viability value over 90%. In the following tests directed to the effect of seed sowing density, the amounts of the seeds were adjusted by directly weighing the seeds.

II. Formulation of the Sowing Medium:

Aside from the fact that sucrose and potato paste were used in different amounts in tests directed to the effect of medium components, all the sowing media included the following components: Knudson C (1946) salts (Knudson, L. (1946), *Amer. Orchid Soc. Bull.* 15: 214–217), sucrose (20 g/L) and potato paste (34 g/L). For the preparation of a solid culture medium, Difco Bacto-agar (8 g/L) was further added. The culture media were adjusted to have a pH value of 5.3, followed by sterilization in an autoclave at 121° C. for 15 minutes.

III. Culture Environment:

The culture room was set at a temperature of 24±2° C., illuminated with cool white fluorescent lamps (TFC FL40D/38) to provide 35±5 $\mu mol \cdot m^{-2} \cdot s^{-1}$ PPFD and cycles of photoperiods and dark periods alternating every 6 hours, i.e., a 12-hour exposure to light each day.

IV. Test Method:

(1) The Effects of Sowing Density on the Growth of Orchid Seedlings

Orchid seeds were weighed under sterile conditions, and then added into a liquid medium to form a seed suspension stock of 1.5 mg/ml. Three treatments of different seed densities were conducted as followed: Taking 1 ml, 2 ml and 3 ml of the seed suspension stock and mixing the same with 9 ml, 8 ml and 7 ml of liquid medium, respectively, so that the resultant seed suspensions for sowing have total amounts of 10 ml containing 1.5 mg, 3.0 mg and 4.5 mg of seeds, respectively. In the sowing stage, sterile plastic petri dishes with an inner diameter of 8.7 cm and a height of 1.25 cm were used as the culture containers. After addition of the seed suspensions thus prepared, the petri dishes were sealed with paraffin films. Each treatment was conducted in triplicate. The seedlings grown after sowing were observed for changes in diameter each week for a total of five weeks.

(2) Effects of the Volumes of Liquid Media and the Manners of Sealing Materials on the Growth of Orchid Seedlings To each of 4 ml, 9 m, 14 ml, 19 ml, and 24 ml of the liquid medium, 1 ml of the aforesaid suspension stock was added so that the resultant seed suspensions respectively had a total volume of 5 ml, 10 ml, 15 ml, 20 m, and 25 ml, while containing 1.5 mg of seeds therein. After addition of the seed suspensions thus prepared, the petri dishes with different volumes of culture media were sealed in three different ways: using two layers of air-permeable film (Micropore™ surgical tape, 3M Company) to seal around the entire outer periphery of the petri dish; using two layers of air-permeable film to seal around one half of the outer periphery of the petri dish and two layers of paraffin film (parafilm "M"®, American National Can™/Menasha Wis. 54952) to seal around the other half of the outer periphery of the petri dish; and using two layers of paraffin film to seal the entire outer periphery of the petri dish. Each sealing treatment was conducted in triplicate. There were altogether 45 petri dishes (5 treatments of different medium amounts×3 sealing treatments×triplicate). Glass flasks having orchid seeds sown on solid culture medium contained therein and sealed with a rubber stopper served as a control group, also conducted in triplicate. After three months of cultivation, the seedlings were observed in terms of growth, and were subsequently dried at 60° C. for 48 hours, followed by measurement of their dry weights.

In another experiment, the petri dishes with orchid seeds in liquid medium were first sealed with two layers of paraffin film and then subjected to static liquid culture for 30 days. Thereafter, one set of the petri dishes were changed to be sealed with 3M Micropore™ surgical tape, and all the petri dishes were subjected to static liquid culture for further 20 days, followed by observing the growth of the seedlings.

(3) Effects of Added Amounts of Potato Paste and Sucrose on the Growth of Orchid Seedlings The liquid medium was prepared based on Knudson C (1946) salts. Potato paste and sucrose were added thereto in amounts listed in Table 1, respectively. The solid culture medium contained Knudson C (1946) salts, sucrose (20 g/L), potato paste (34 g/L), and Difco Bacto-agar (8 g/L). The culture media were adjusted to have a pH value of 5.3, followed by sterilization in an autoclave at 121° C. for 15 minutes. Reverse-osmosis water with a pH value of 5.3 before sterilization was used as a control.

TABLE 1

Codes for culture media and added amounts of potato paste and sucrose

| | Culture medium | | | | | | | | |
|---|---|---|---|---|---|---|---|---|---|
| | P1 | P2 | P3 | P4 | S1 | S2 | S3 | S4 | S5 |
| Sucrose (g/L) | 20 | 20 | 20 | 20 | 0 | 10 | 20 | 30 | 40 |
| Potato paste (g/L) | 0 | 17 | 34 | 68 | 17 | 17 | 17 | 17 | 17 |

Orchid seeds were weighed under sterile conditions, and then added into sterilized water to form a seed suspension stock of 15 mg seeds/ml water. To each of 20 ml of the nine media shown above was added 0.1 ml of the seed suspension stock. The nine seed suspensions thus prepared were added into sterile plastic petri dishes with an inner diameter of 8.7 cm and a height of 1.25 cm, respectively. Thereafter, the petri dishes were sealed with two layers of paraffin film. The solid culture medium and purified water were used as controls. Each treatment was conducted in triplicate. The seedlings grown after sowing were observed for changes in diameter each week for a total of seven weeks.

V. Results:

(1) Effects of Seed Sowing Density on the Growth of Orchid Seedlings

Referring to FIG. 1, as compared to those sown in solid culture medium, the seedlings grown from *Phalaenopsis* seeds 60 days after sowing in liquid medium exhibited good and uniform growth, and no chlorosis was observed.

Figure 2:
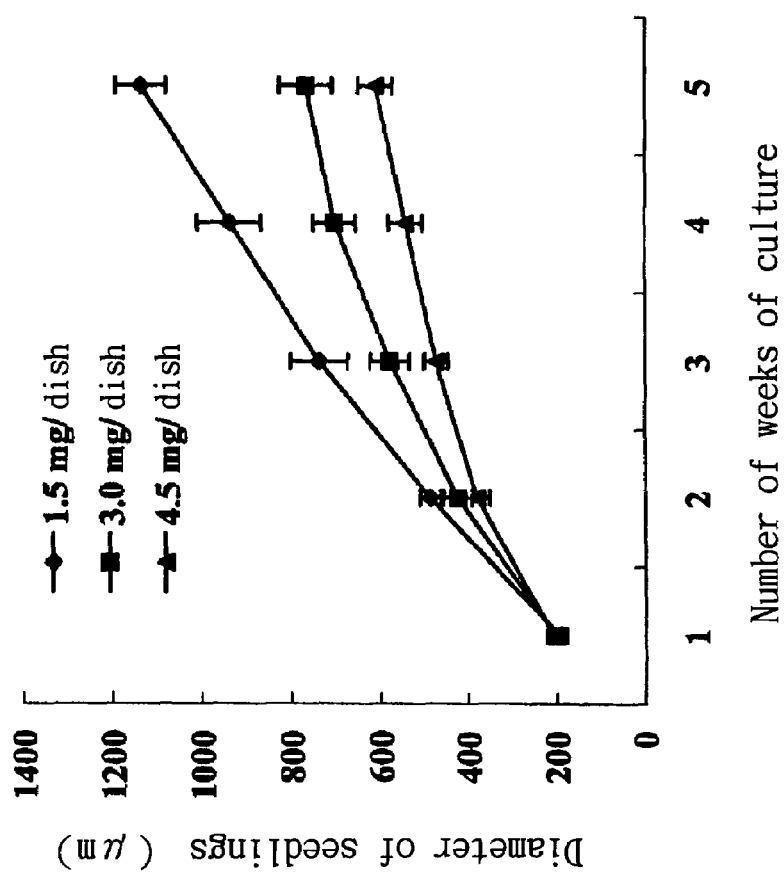
FIG. 2 shows the effects of sowing density on the growth of *Phalaenopsis* seedlings.

In addition, three different amounts of seeds sown in media of the same amount resulted in seed germination rates of no significant difference. However, the growth rate of the seedlings decreased with the rise in seed sowing density (FIG. 2). When a petri dish with an inner diameter of 8.7 cm was used as a culture container, the optimal amount of seeds for sowing was about 1.5 mg.

(2) Effects of the Volumes of Liquid Media and the Manners of Sealing Culture Containers on the Growth of Orchid Seedlings In the experiment using three different sealing treatments in combination with 5 different amounts of the liquid media, the results show that the water levels of the media dropped with an increase in culture time. For petri dishes sealed with air-permeable film and those sealed with both air-permeable film and paraffin film, all the media of the cultures dried up due to loss of water within 40 days and within 2 months, respectively. Curling of the rhizoids and death of the seedlings were also observed due to loss of water. Besides, all of the seedlings did not reach the shoot development stage according to the standards of subculture (data not shown). As for petri dishes sealed with paraffin film, all the cultures did not exhibit dryness during the three-month culture period. The growth results of the seedlings are shown in Table 2. When petri dishes were added with liquid medium in an amount of 20 ml, no further addition of the medium was required during the three-month growth period, and best growth of orchid seedlings was observed in these petri dishes.

TABLE 2

The effects of the volumes of liquid media on the growth of seedlings three months after sowing

|  |  | Volumes of liquid medium | | | | | Solid medium |
|---|---|---|---|---|---|---|---|
|  |  | 5 ml | 10 ml | 15 ml | 20 ml | 25 ml |  |
| Growth stages of seedlings* | Mortality (%) | 0.7 b** | 2.3 a | 2.3 a | 1.7 a | 2.3ª | 0.7 b |
|  | Stage 1 (%) | 29.3 a | 11.7 b | 6.3 bc | 0 c | 1 c | 21 a |
|  | Stage 2 (%) | 70 cd | 78.3 bc | 84.7 b | 95 ab | 87.7 a | 63 d |
|  | Stage 3 (%) | 0 d | 7.7 ab | 6.7 b | 3.3 c | 9 cd | 10 a |
| Weight of 50 seedlings | Fresh wt. (mg) | 82 e | 243 c | 543 b | 575 ab | 623 a | 189 d |
|  | Dry wt. (mg) | 3.2 d | 10.2 c | 22.9 a | 25.2 a | 23.9 a | 12.8 b |
|  | Dry/fresh wt. (%) | 3.9 c | 4.2 bc | 4.2 bc | 4.4 b | 3.8 c | 6.7 a |

*Stage 1: heart-shaped to torpedo embryo
Stage 2: first leaf smaller than 3 mm
Stage 3: first leaf larger than 3 mm
**Different letters within a row present significant differences at P = 0.05 level by Duncan's multiple range test.

Figure 3:
FIG. 3 shows the growth results of *Phalaenopsis* seedlings after being subjected to static culture for 50 days in petri dishes sealed with a sealing material subsequent to sowing of *Phalaenopsis* seeds in a liquid medium, in which the petri dish shown in the left panel was maintained to be sealed with a paraffin film during the 50 days of culture, whereas the seal material of the petri dish shown in the right panel was changed from paraffin film to 3M micropore tape after 30 days of culture.

In another experimental test, orchid seeds were sown in petri dishes containing liquid medium. Thereafter, the petri dishes were sealed with paraffin film and subjected to static liquid culture for 30 days, followed by sealing with 3M Micropore™ surgical tape for a further static liquid culture for 20 days. The growth results of the seedlings are shown in FIG. 3.

Paraffin film is air-permeable but water-impermeable, and 3M Micropore™ surgical tape is both air-permeable and water-permeable. The applicants found that when two different sealing materials were used in sequence in sealing the petri dishes during static liquid culture, significant beneficial effects upon the growth of seedlings were observed.

Figure 4:
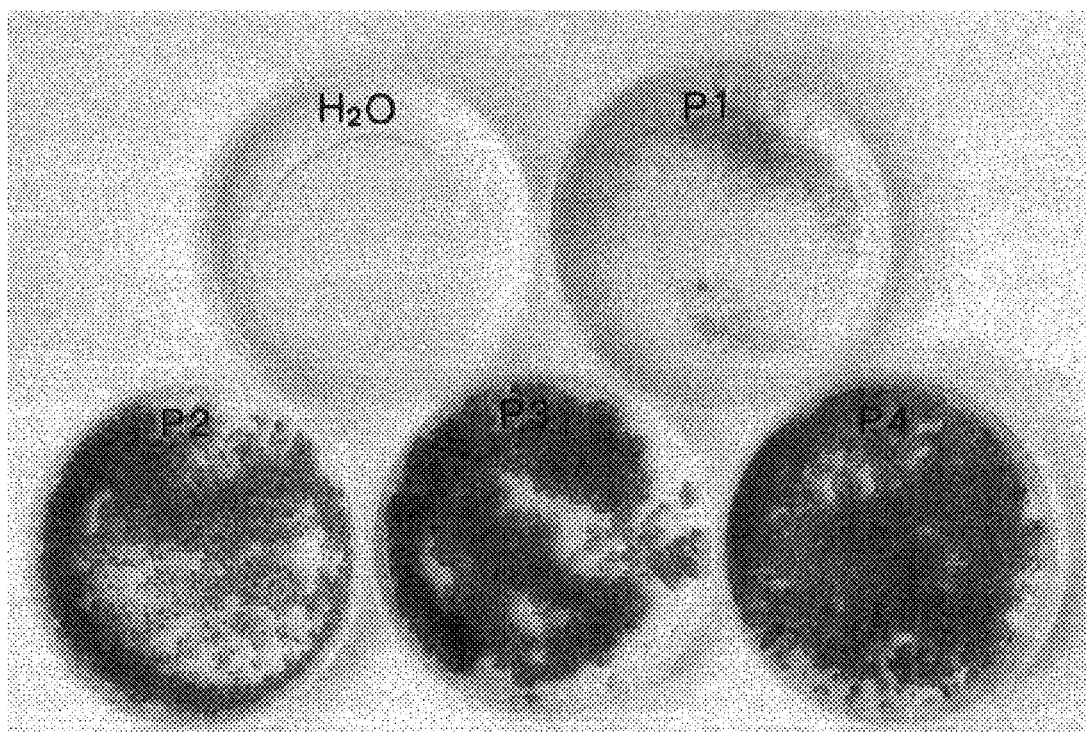
FIG. 4 shows the effects of the addition of potato paste on the growth of *Phalaenopsis* seedlings that were developed 30 days after sowing.
Figure 5:
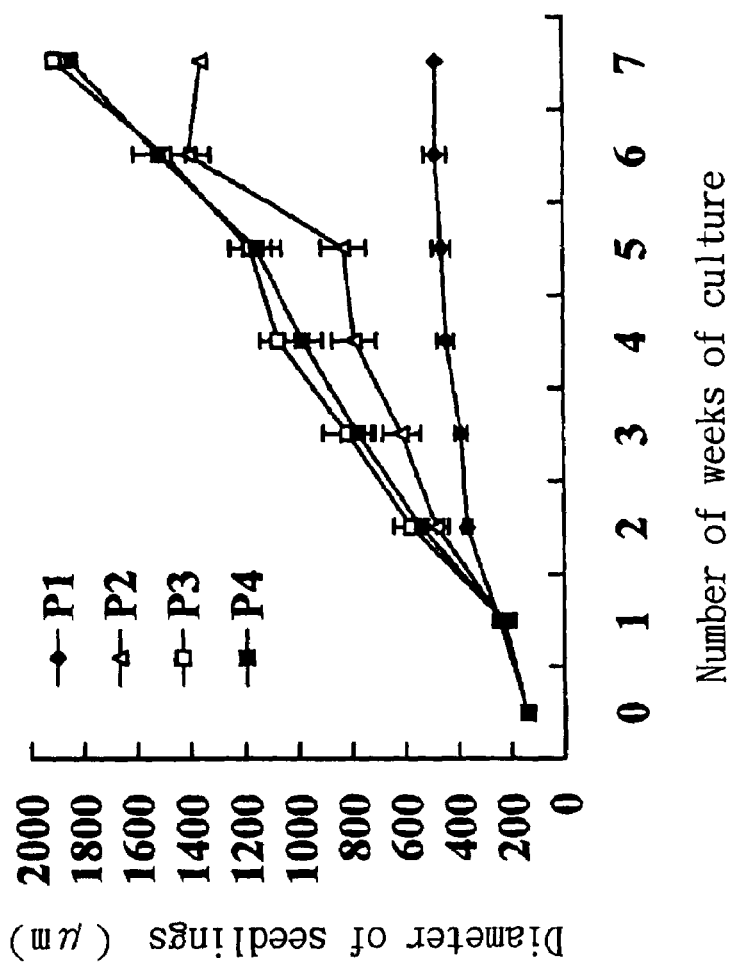
FIG. 5 shows the effects of added amounts of potato paste on the growth of *Phalaenopsis* seedlings.

(3) Effects of Added Amounts of Potato Paste and Sucrose in Liquid Media on the Growth of Orchid Seedlings Referring to FIGS. 4 and 5, *Phalaenopsis* seeds did not germinate in purified water. In the experimental group using a liquid medium containing sucrose without addition of potato paste (group P1), the growth of the seedlings slowed down 2 weeks after sowing, and the seedlings did not turn green 30 days after sowing. By week 7, all the seedlings died of chlorosis. Addition of potato paste could promote the growth of the seedlings. However, if the potato paste was added in an amount of 34 or 68 g/L, no significant difference in the growth of seedlings was observed. The seedlings grown in culture media of groups P2, P3 and P4 turned green by weeks 3, 2 and 2, respectively.

Figure 6:
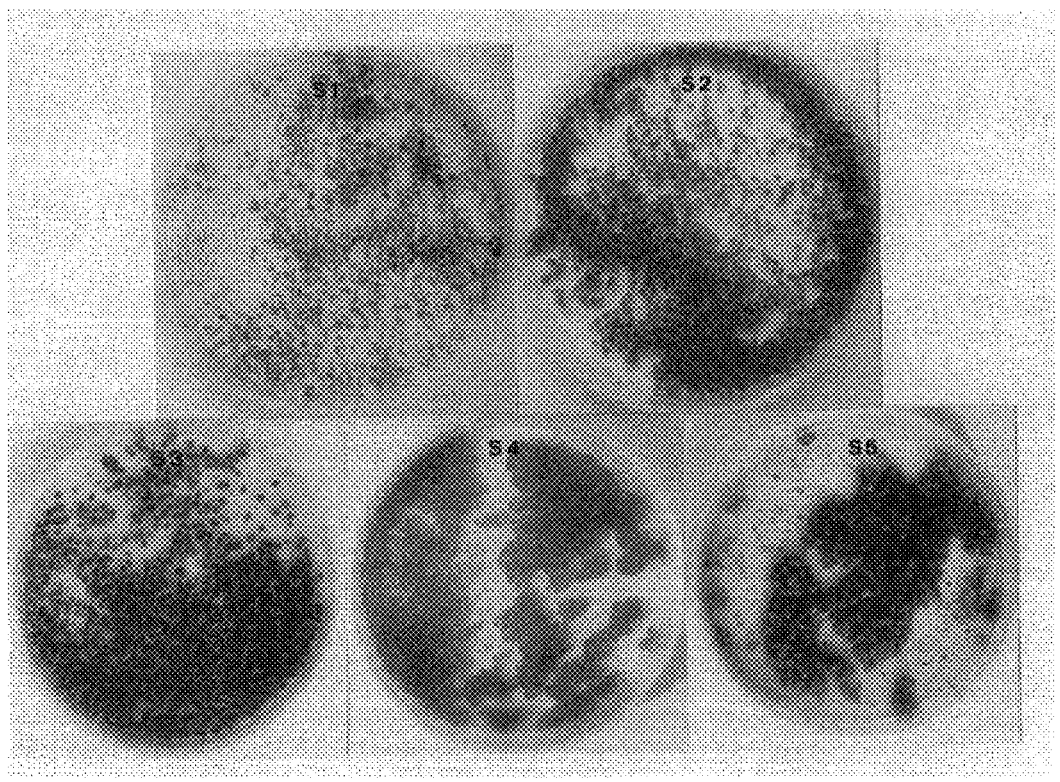
FIG. 6 shows the effects of the addition of sucrose on the growth of *Phalaenopsis* seedlings that were developed 30 days after sowing.
Figure 7:
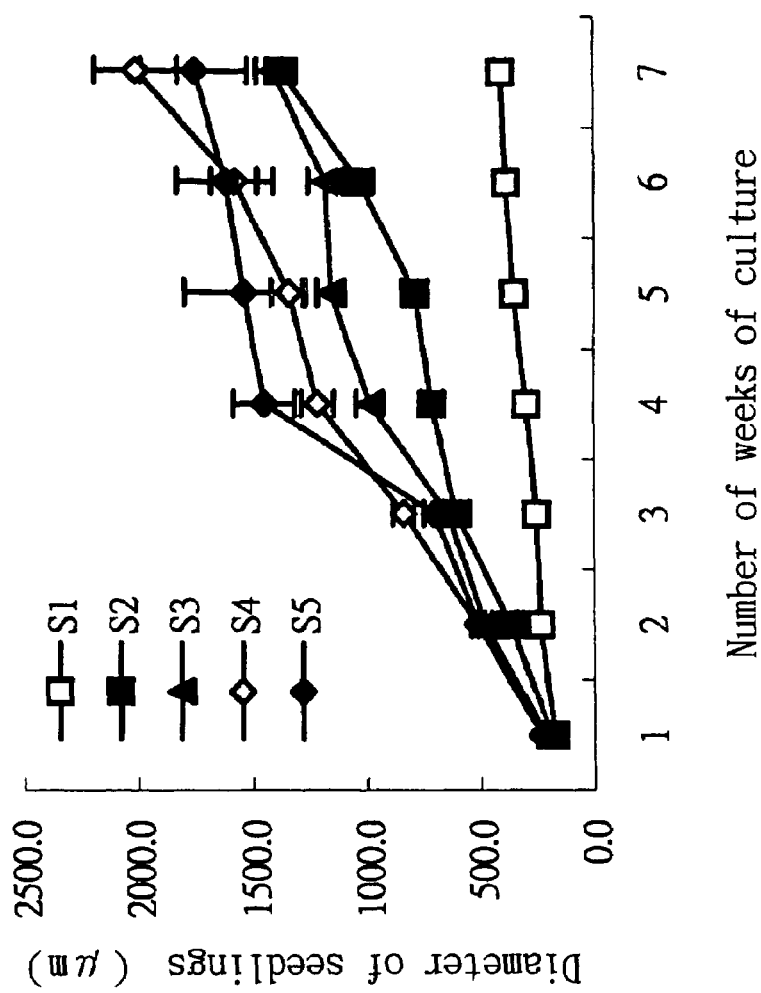
FIG. 7 shows the effects of added amounts of sucrose on the growth of *Phalaenopsis* seedlings.

As shown in FIGS. 6 and 7, in the experimental group using a liquid medium containing potato paste in an amount of 17 g/L without addition of sucrose (group S1), the growth of the seedlings slowed down 2 weeks after sowing, and the seedlings turned light green. The growth rates of seedlings grown in the liquid media of groups S2, S3 and S4 became higher with an increase in sucrose concentration. When sucrose was added in an amount of 40 g/L, significant differences in the growth of seedlings were observed starting from the fourth week of culture, and there was a death rate of 23% by week 7.

The above results show that optimal growth of orchid seedlings was observed in experimental groups using a liquid medium containing 34 g/L potato paste and 20 g/L sucrose or a liquid medium containing 17 g/L potato paste and 30 g/L sucrose. The addition of potato paste could promote the seedlings to turn green.

The above experiments show that when equal amounts of liquid media were used for sowing seeds in different densities, there was no significant difference in seed germination rate. However, the growth rate of the seedlings slowed down with the rise in the seed sowing density (FIG. 2). This indicates that nutrient competition is an important factor affecting the growth of the seedlings after germination. When media of different depths were used for sowing, although the seeds sank to the bottom of the media, the seed germination rate was not affected. On the other hand, the seeds did not germinate when cultured in water, which indicates that orchid seeds need nutrients more than oxygen for germination.

When different sealing means were used in conducting liquid suspension sowing, the growth of seedlings in the experimental groups using air-permeable tape as the sealing means was faster than the growth of seedlings in experimental groups using paraffin film as the sealing means. However, the former experimental groups have a drawback in that frequent addition of water was needed. Therefore, adequate nutrients have to be provided at the initial stage of liquid suspension sowing. After germination, ventilation has to be considered in order to promote the growth of seedlings.

As compared to prior known methodologies, which involved the use phloroglucinol (Phan, C. T. and P. Hegedus (1986), supra) or cold treatment (Phan, C. T. and P. Hegedus (1986), supra) to recover vitrificated explants so as to restore their normal growth functions, or which tried to avoid the occurrence of vitrificated explants by reducing cytokinin concentration, increasing agar amount, or enhancing air exchange in culture containers, this invention prevents the cultivated orchid seedlings from vitrification by controlling the depth of culture medium in combination with the use of a sealing means to seal the culture container so as to enable the depth of the culture medium to drop slowly. This is the simplest and the most cost-efficient method. The experiments show that when a petri dish with a 9 cm diameter was used as the culture container, and a culture medium of 20 ml was used to cultivate 1.5 mg seeds (approximately 750±50 seeds), supplement of additional medium was not required during a culture period of 75 days, and the seedlings were observed to have a more uniform and better growth as compared to those grown on solid culture (Table 2).

In the experimental group using a culture medium containing sucrose without addition of potato paste (group P1), the seedlings failed to turn green (FIG. 5) and died of chlorosis by week 7. However, in the experimental group using a culture medium containing potato paste without addition of sucrose (group S1), the growth of seedlings slowed down, and the seedlings became greenish in color two weeks after sowing (FIG. 7). This indicates that Phalaenopsis seedlings need potato paste to promote the synthesis of chlorophyll, and potato paste cannot be substituted by sucrose.

Example 2

Liquid Culture at the Stage of Subculture

I. Preparation of Culture Medium:

The components used in the culture medium for subculture include: 1/4MS salts, sucrose (20 g/L), and potato paste (34 g/L). For the preparation of a solid culture medium, Difco Bacto-agar (8 g/L) was further added. The culture medium was adjusted to have a pH value of 5.3, followed by sterilization in an autoclave at 121° C. for 15 minutes.

II. Test Method:

When the orchid seedlings developed from the static liquid culture described above were observed to have first leaves (around 75 days after sowing), they were further subjected to subculture in a liquid medium using Magenta GA7 as culture containers, installed with or without a support therein. Conventional glass flasks having orchid seedlings cultivated on solid culture medium contained therein served as a control group. The treatment groups are listed in Table 3. Each treatment was conducted in triplicate. The seedlings were observed in terms of the growth of leaves and roots on Day 45 and Day 75 of the subculture period, respectively. After 45 days of subculture, plantlets in one of the containers in treatment group L1 and plantlets in one of the containers in treatment group S were transferred to flasks containing solid culture medium, respectively. Cultivation of orchid seedlings in the rest of the culture containers was continued until Day 75. Twenty-five plantlets were randomly selected from each culture container, and their fresh weight was measured. These plantlets were then dried in an oven at 60° C. for 48 hours, and their dry weight was measured.

TABLE 3

Culture conditions at the stage of subculture

| | Treatment | | | | |
|---|---|---|---|---|---|
| | L1 | L2 | LR | LN | S |
| Culture container | GA7 | GA7 | GA7 | GA7 | 600 ml flask |
| Support | none | none | Plastic raft | Non-woven fabric and paper towel | Agar |
| Culture medium (ml) | 20 | 40 | 50 | 40 | 100 |
| Number of seedlings | 36 | 72 | 36 | 36 | 90 |

III. Results:

Liquid medium was used in conducting the subculture of orchid seedlings, and the growth results of orchid seedlings in different treatment groups after 45 days of subculture are shown in Table 4.

For treatment groups using liquid medium, the average number of leaves and the lengths of the first and second leaves were greater than those obtained in the control group using solid culture medium. In addition, in the treatment groups in which liquid medium was used and no support was installed in the culture container (groups L1 and L2), most of the seedlings developed two leaves, and their leaves were longer than those in the treatment groups using supports (groups LR and LN). The greatest number of roots was observed in the treatment group in which nonwoven fabric and paper towel were used as the support, whereas the longest root was observed in the treatment group in which plastic rafts were used as the support. At this juncture, plantlets developed in one culture container of the treatment group L1 and plantlets developed in one culture container of the treatment group S were transferred to flasks containing solid culture medium for further subculture, respectively. One month later, the difference in growth of the plantlets became more obvious between the two treatment groups (see FIGS. 9 to 11).

TABLE 4

The growth results of orchid seedlings after 45 days of subculture

| Treatment | Seedling growth (%) | | | Leaf length (mm) | | Root | |
|---|---|---|---|---|---|---|---|
| | leafless | one leaf | two leaves | 1st leaf | 2nd leaf | Number of roots | length (mm) |
| L1 | 2.5 c* | 12.5 c | 85.0 a | 4.6 bc | 3.3 a | 0.43 b | 3.9 ab |
| L2 | 7.5 b | 16.3 c | 76.2 a | 5.4 a | 3.1 a | 0.43 b | 2.8 b |
| LR | 0 c | 72.2 b | 27.8 b | 4.4 c | 2.4 b | 0.45 b | 5.1 a |
| LN | 0 c | 97.2 a | 2.8 c | 5.1 ab | 2.7 b | 0.75 a | 4.1 ab |
| S | 23.0 a | 75.0 b | 2.0 c | 2.5 d | 1.0 c | 0.43 b | 3.3 b |

*Different letters within a column present significant differences at $P = 0.05$ level by Duncan's multiple range test.

After being subcultured for 75 days, orchid seedlings in the treatment groups using liquid medium were observed to have better leaf growth as compared to those in the treatment groups using solid culture medium (see Table 5).

In the treatment group L1, most of the seedlings were observed to have developed three leaves, as well as highest fresh weight, dry weight and dry weight to fresh weight ratio, and their growth being the best. However, the measured root length of the treatment group L1 was not different from those of the treatment groups in which a support was used during the subculture.

As for the treatment group L2, while the seedlings subcultured therein were observed to have the least number of roots and the shortest root length, the length of their leaves was not significantly different from that of seedlings in treatment groups using a support during subculture. Moreover, their leaves became thick and their roots exhibited a brownish black color.

TABLE 5

The growth results of orchid seedlings after 75 days of subculture

| Treatment | Seedling growth (%) | | | Leaf length (mm) | | | Root number | Root length (mm) | Fresh wt. (g) | Dry wt. (g) | Dry wt./ fresh wt. (%) |
|---|---|---|---|---|---|---|---|---|---|---|---|
| | One leaf | Two leaves | three leaves | 1st leaf | 2nd leaf | 3rd leaf | | | | | |
| L1* | 0 c** | 22 c | 78 a | 12.8 a | 9.2 a | 8.6 a | 1.0 b | 11.5 a | 3.88 a | 0.47 a | 12.1 a |
| L2 | 0 c | 84 a | 16 b | 7.4 bc | 6.4 b | 4.5 b | 0.8 c | 3.8 c | 2.74 b | 0.30 b | 10.9 a |
| LR | 22 b | 78 a | 0 c | 8.6 b | 5.6 bc | 0 c | 1.2 a | 11.6 a | 2.51 b | 0.14 c | 5.6 b |
| LN | 43 a | 57 b | 0 c | 7.9 bc | 5.0 c | 0 c | 1.0 b | 10.8 a | 1.73 c | 0.10 c | 5.8 b |
| S | 43 a | 57 b | 0 c | 6.7 d | 3.6 d | 0 c | 1.0 b | 7.3 b | 1.19 c | 0.06 c | 5.0 b |

*Twenty milliliter of liquid media was added on the 45$^{th}$ day.
**Different letters within a column present significant differences at P = 0.05 level by Duncan's multiple range test.

Orchid seedlings developed from static liquid culture 75 days after sowing were subjected to subculture. After 45 days of subculture, the orchid seedlings in the treatment groups using liquid medium were observed to have better and faster leaf growth as well as more uniform growth, and none of the seedlings was found to develop vitrification. In addition, the results obtained in the treatment groups without the use of a support during the static liquid culture were better than those of the treatment groups using a support during the static liquid culture (see Table 4). This proved the feasibility of conducting subculture in liquid medium in the absence of a support. In the treatment groups that do not use a support, the seedlings floated on the liquid surface of the medium, and the drop of the liquid surface of the medium was faster than that in the treatment groups using a support, which may be the main factor for preventing occurrence of vitrification. In addition, as the whole bodies of the seedlings were in contact with the liquid medium, the medium absorption area thereof could be increased, thereby promoting growth of the seedlings.

With respect to the treatment groups L1 and L2, no significant difference in growth was observed between the seedlings of the two treatment groups after 45 days of subculture. However, after 75 days of subculture, the seedlings' growth in the treatment group L2 significantly slowed down (see Table 5). Besides, their leaves became thick and their roots became blackish, while the culture medium turned brownish. This might be due to the facts that the leaves' need for oxygen increased with growth, and that a relatively large number of seedlings were subcultured in the treatment group L2 such that some could not rise to the liquid surface of the medium, thereby resulting in deficiency in oxygen and generation of ethylene and phenolic compounds that caused abnormal growth of the seedlings. Therefore, when conducting liquid culture of *Phalaenopsis* seedlings in a supportless liquid medium, the effect of liquid surface area on the growth of the seedlings might be more important than that of liquid level. As for seedlings cultivated in the presence of plastic rafts, there were more and longer roots after 75 days of subculture (see Table 5). This was because the liquid surface of the medium dropped below the level of the water-permeable film, which might possibly stimulate the growth of roots.

For seedlings cultivated in the treatment group L1, the liquid medium almost dried up 45 days after subculture. Although supplement of additional culture medium at this juncture could result in the optimal growth of the seedlings, it is rather laborious. When the seedlings were transferred to flasks containing solid culture medium for further subculture, 30 days later, the seedlings' growth was significantly better than that of the control group using solid culture medium (see FIG. 9). Therefore, it is recommended that the seedlings be transferred after being subcultured in a supportless liquid medium for 45 days. This would not require supplementation of additional culture medium and can avoid browning of the culture medium, while ensuring the optimal growth of seedlings.

Figure 8:
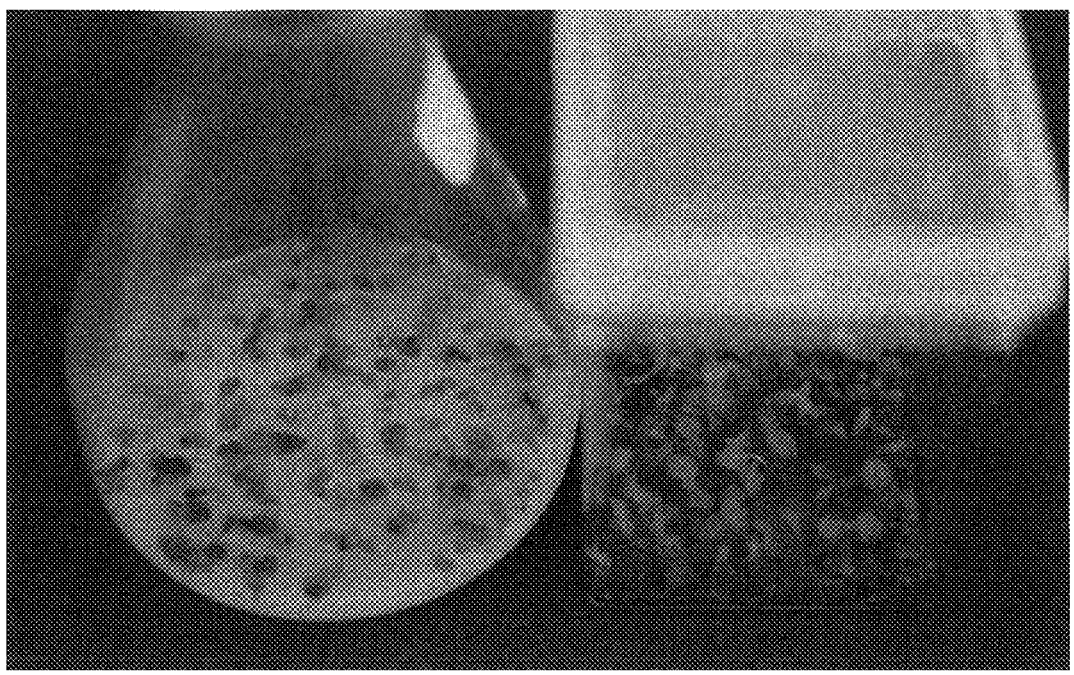
FIG. 8 shows the growth results of *Phalaenopsis* seedlings, which were developed for 75 days after sowing and then subjected to a further subculture treatment for 45 days, in which the left panel shows *Phalaenopsis* seedlings cultivated in solid culture medium (control group, corresponding to the group S shown in Table 3 hereinbelow), whereas the right panel shows *Phalaenopsis* seedlings cultivated in a static liquid culture according to this invention (experimental group, corresponding to the group L1 shown in Table 3 hereinbelow)
Figure 9:
FIGS. 9, 10 and 11 respectively show the growth results of *Phalaenopsis* explants (i.e. the developed *Phalaenopsis* seedlings shown in FIG. 8 after a subculture treatment of 45 days) after being set for planting in a solid culture medium for 30 days, 60 days and 120 days, in which the left panels show *Phalaenopsis* explants cultivated in a solid culture medium (control group, corresponding to the group S shown in Table 3 hereinbelow), whereas the right panels show *Phalaenopsis* explants cultivated in a static liquid culture according to this invention (experimental group, corresponding to the group L1 shown in Table 3 hereinbelow).
Figure 10:
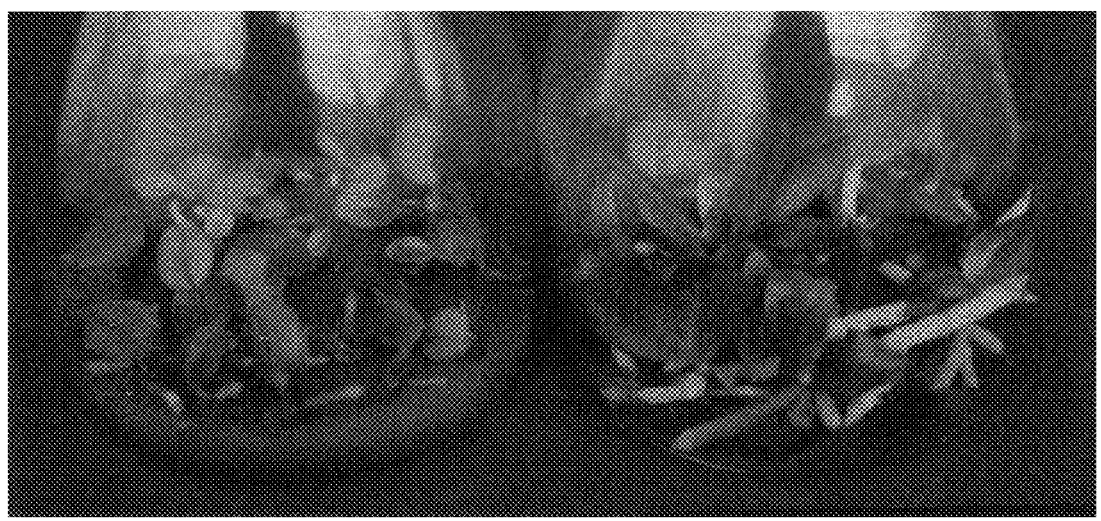
Figure 11:

FIGS. 9 to 11 further show the growth results of *Phalaenopsis* explants (i.e. the developed *Phalaenopsis* seedlings shown in FIG. 8 after a subculture treatment of 45 days) after being set for planting in a solid culture medium for 30 days, 60 days and 120 days, respectively.

The above experiments show that when orchid seedlings, which were produced by static liquid culture 75 days after sowing, were subjected to subculture in a liquid medium using GA7 as containers, with or without supports, such seedlings were observed to have a faster growth of shoots, as compared to orchid seedlings continuously cultivated on a solid culture medium after sowing. However, the seedlings developed more and longer roots when they were subjected to subculture using a liquid medium in the presence of a support. Growth was best and uniform when 36 seedlings were placed in 20 ml of a supportless liquid medium. The culture period from sowing seeds to developing seedlings with two leaves can be shortened by at least 1.5 months using the process of static liquid culture according to this invention, as compared to the conventional solid culture techniques.

Evidently, according to this invention, the use of liquid suspension sowing and liquid subculture can increase the growth rate and the dry weight/fresh weight ratio of orchid seedlings. It is estimated that the culture period can be shortened by about 45 days or more using the process of static liquid culture according to this invention, as compared to the conventional solid culture techniques using solid culture media in flasks. Therefore, it is proven herein that the process of static liquid culture according to this invention can be applied to the production of orchid seedlings in two stages.

All patents and literature references cited in the present specification are hereby incorporated by reference in their entirety. In case of conflict, the present description, including definitions, will prevail.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

We claim:

1. A process for producing orchid seedlings by static liquid culture, comprising:
   (a) suspending a suitable amount of orchid seeds in a liquid medium suitable for germination and growth of the orchid seeds to form a seed suspension; and
   (b) adding the seed suspension obtained in step (a) into an empty culture container having a bottom wall to allow the seed suspension within the culture container to have a predetermined depth sufficient to enable each of the seeds to be suspended within the liquid medium while not subjecting any seed closest to the bottom wall of the culture container to an oxygen-deficient state, for the suspended seeds to germinate and grow.

2. The process according to claim 1, the process being used to produce *Phalaenopsis* seedlings.

3. The process according to claim 1, wherein the culture container used in step (b) is a petri dish with a cover.

4. The process according to claim 1, wherein the seed suspension added to the culture container in step (b) has a predetermined depth of not greater than 1 cm, as measured from the bottom of the culture container.

5. The process according to claim 4, wherein the seed suspension added to the culture container in step (b) has a predetermined depth within the range of approximately 0.1–1.0 cm, as measured from the bottom of the culture container.

6. The process according to claim 1, wherein the seed suspension obtained in step (a) has a sowing density not greater than 113±9 seeds/ml of culture medium.

7. The process according to claim 1, further comprising a step (c) of subjecting the culture container to a standing treatment to allow the seeds suspended within the liquid medium to germinate and grow into seedlings.

8. The process according to claim 7, wherein, between step (b) and step (c), an additional step of using a sealing material to seal the culture container is conducted to retard evaporation of water moisture from the seed suspension added into the culture container.

9. The process according to claim 8, wherein the sealing material used in the additional step is selected from a group consisting of paraffin film, air-permeable tape, and a combination thereof.

10. The process according to claim 2, wherein after being subjected to the standing treatment of step (c), the orchid seeds suspended within the liquid medium germinate and grow into seedlings having first leaves not larger than 0.4 cm.

11. The process according to claim 10, wherein the seedlings grown in step (c) are subject to further cultivation by the following steps:
    (d) placing the seedlings grown in step (c) into a culture container having a bottom wall and containing a liquid medium suitable for growth of orchid seedlings such that the liquid medium in the culture container has a predetermined depth sufficient to enable each of the seedlings to be suspended in the liquid medium while not subjecting any seedling closest to the bottom wall of the culture container to an oxygen-deficient state; and
    (e) subjecting the culture container to a standing treatment to allow the seedlings suspended in the liquid medium to grow further.

12. The process according to claim 11, wherein the liquid medium added to the culture container in step (d) has a predetermined depth of not greater than 1.6 cm, as measured from the bottom of the culture container.

13. The process according to claim 12, wherein the liquid medium added to the culture container in step (d) has a predetermined depth within the range of approximately 0.2–1.5 cm as measured from the bottom of the culture container.

14. The process according to claim 11, wherein, after being subjected to the standing treatment of step (e), the seedlings grown in step (c) grow into seedlings having about two leaves.

* * * * *